June 22, 1976
A. HREBENIUK
POINSETTIA PLANT
Filed March 20, 1975
Plant Pat. 3,917
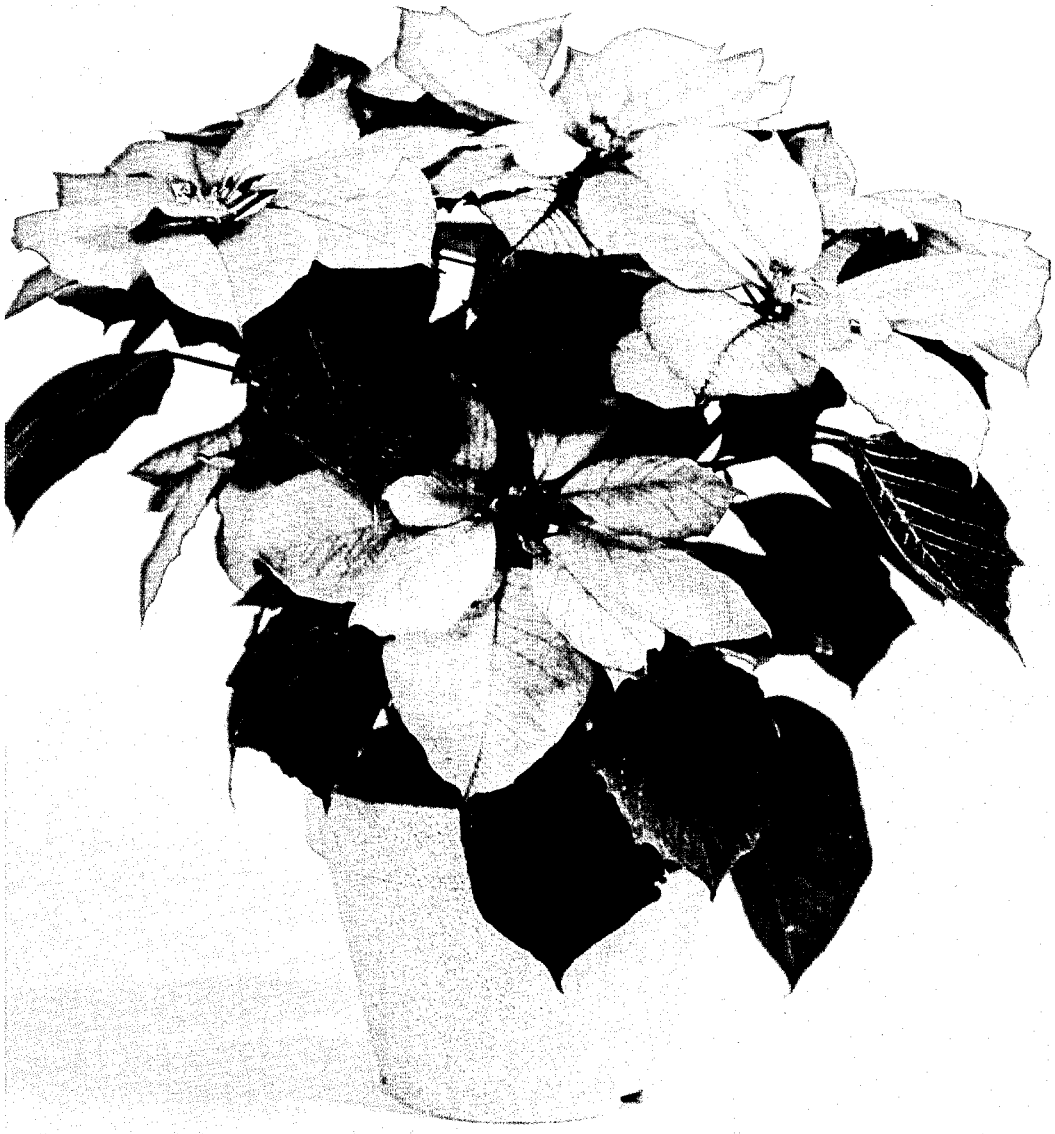

United States Patent

Plant Pat. 3,917
Patented June 22, 1976

1

3,917

POINSETTIA PLANT

Alexander Hrebeniuk, 7 Corner Road,
Perkasie, Pa. 18944

Filed Mar. 20, 1975, Ser. No. 560,227
Int. Cl. A01h *5/00*
U.S. Cl. Plt.—86 1 Claim This invention relates to marketable poinsettia plants of the species *Euphorbia pulcherrima.*

The present invention is for a new and distinct variety of poinsettia plant of the species *Euphorbia pulcherrima,* produced and originated by cross-breeding two different red seedlings with the definite goal of creating a new strong-growing and free-branching poinsettia plant variety which is hardy at relatively cool temperatures.

In selecting poinsettia plants for breeding, it was a primary object that the final result give the horticultural industry a new poinsettia plant which is commercially desirable. This new poinsettia plant is suitable for pot growth production that would branch freely, have a very compact habit that would obviate the need for chemical height control, be resistant to "dark spotting" when watered, and be resistant to fade with changes in temperature. A highly commercially advantageous feature of the invention is that the new poinsettia plant can be grown in relatively cool temperatures, preferably 58° F., but within a range of 50° F. to 60° F. When the plant has bloomed, its beauty and life can be held for about two months by maintaining the plant at a temperature of 50° F. All of these objects were achieved by this distinct new variety that distinguishes itself from both its parents.

I have now produced and disclose herein a new, compact plant with desirable characteristics:

(1) A new plant that has the ability to produce 10 branches from a single pinched plant without chemical treatment.

(2) A new plant which can be initially raised at 58° F. temperature, which temperature can be lowered to 50° F. when bloomed.

(3) A new plant which can start blooming before Christmas, as early as the second week of November, stay bloomed for two months, all without loose foliage or loose flowers.

(4) A new poinsettia plant which has double flowers which are resistant to fade.

(5) A new poinsettia plant which produces double flowers, as particularly contrasted with those poinsettia plants which yield single or triple flowers.

(6) A new poinsettia plant which can be watered without "dark spotting" resulting therefrom.

(7) A new poinsettia plant which has hardy foliage which is resistant to drooping.

The accompanying photograph shows a typical specimen of my new variety with the colors being reproduced as closely as available photographic methods can define. The colors in this photograph and appended descriptive material are coded from Exotica Horticultural Color Guide, located at pages 37 and 38 of Exotica 3 Pictorial Cyclopedia of Exotic Plants (Century Edition) by Alfred Byrd Graf, published 1970 by Roehrs Company—Library of

2

Congress Catalog Card No. 74-92881—except where common dictionary significance will be obvious. The Exotica Color Guide determinations, as stated at page 38, approximate Maerz and Paul "Dictionary of Color" and Royal Horticultural Society Colour Charts.

The description and photograph are taken from specimens asexually reproduced under my direction through natural growth at Perkasie in Pennsylvania, U.S.A.

Parentage: Seedling.

*Seed parent.*—A selected red seedling of unknown parentage of the Rudolph family (an unpatented type developed by the University of Maryland).

*Pollen parent.*—A selected red seedling of unknown parentage of the Elizabeth type.

Growth habit: Upright growth with shortened height characteristics suitable for pot culture, obviating the need for chemical growth regulators. A distinctive growth characteristic of this plant is its ability to make 4 to 10 branches from a single pinched plant.

Rooting habit: Very fast. The roots develop within two weeks and are rot resistant.

Temperature: The new poinsettia plant can be grown in cool temperatures, as low as 50° F., preferably 58° F., yielding a hardy, beautiful plant. The highest desired growing temperature is 60° F. The plant can be maintained or held for 2 months at a 50° F. temperature.

Blooming season: The new poinsettia plant is of an early eight week variety, starting mostly in the second week of November.

Foliage: The leaves are spaced about the plant, 10 to 20 leaves or more, and are generally short and rounded, unpointed and bow shaped, normally described as obovate in appearance (as described in Exotica). The leaf color on mature leaves is forest green (Code No. 77) on the upper side and meadow green (Code No. 76) on the underside. The ribs and veins are light. The edge is dark and smooth with double serrations. The underside is smooth.

Flowers (Cyathia): Each bract is generally round in shape, being wider than known varieties, the upper side having a flat texture, and the underside having a smooth texture. The color on each side is cherry (Code No. 26). Typically the number of bracts per stem range from 18 to 20. The length of a typical bract, in bloom, is 7 inches, with an overall width of 4¼ inches. The stamens and styles are blood red (Code No. 27). The pollen and nectar cups are canary (Code No. 3).

The new wood of this new variety is dark gray in color, which turns to dark green as the wood ages. The bark is smooth when new, and is rough when old.

I claim:

1. A new and distinct variety of poinsettia plant substantially as illustrated and described, characterized particularly as to novelty by its compact growth, self-branching habit, non-drooping foliage, and its ability to maintain its beauty and life at a temperature range of 50° F. to 60° F.

No references cited.

ROBERT E. BAGWILL, Primary Examiner